United States Patent [19]
Snyder

[11] Patent Number: 6,063,771
[45] Date of Patent: May 16, 2000

[54] FORMULATIONS FOR CONTROLLING HUMAN LICE

[75] Inventor: Daniel Earl Snyder, Indianapolis, Ind.

[73] Assignee: Eli Lilly and Company, Indianapolis, Ind.

[21] Appl. No.: 09/338,116

[22] Filed: Jun. 22, 1999

Related U.S. Application Data

[60] Provisional application No. 60/091,658, Jul. 2, 1998.

[51] Int. Cl.⁷ .................................................. A61K 31/70
[52] U.S. Cl. ............................................. 514/31; 514/881
[58] Field of Search ............................................. 514/310

[56] References Cited

U.S. PATENT DOCUMENTS

| | | | |
|---|---|---|---|
| 4,927,813 | 5/1990 | Bernstein .................................. | 514/65 |
| 5,202,242 | 4/1993 | Mynderse et al. ........................ | 435/76 |
| 5,227,163 | 7/1993 | Eini et al. ............................. | 424/195.1 |
| 5,288,483 | 2/1994 | Cardin et al. ............................. | 424/70 |
| 5,496,931 | 3/1996 | Boeck et al. ............................. | 536/7.1 |
| 5,591,606 | 1/1997 | Turner et al. ............................. | 435/76 |
| 5,767,253 | 6/1998 | Turner et al. ............................. | 536/6.5 |
| 5,840,861 | 11/1998 | Mynderse et al. ..................... | 536/16.8 |

OTHER PUBLICATIONS

CA130:193066, Sparks et al, J. Econ. Entomol., 91(6), 1277–1283, 1998.

CA126:234728, Deamices et al., ACS Sympos. Ser, 658, 144–154, 1997.

C.V. DeAmicis et al. "Physical and Biological Properties of the Spinosyns: Novel Macrolide Pest–Control Agents from Fermentation," American Chemical Society Symposium Series: *Phytochemicals for Pest Control*, Chapter 11, pp. 144–154 (1977).

*Primary Examiner*—Rebecca Cook
*Attorney, Agent, or Firm*—Frederick D. Hunter

[57] ABSTRACT

Safer pediculicidal formulations comprising a spinosyn, or a physiologically acceptable derivative or salt thereof, and a physiologically acceptable carrier, and methods of controlling lice infestations in a human with these formulations are provided.

14 Claims, No Drawings

FORMULATIONS FOR CONTROLLING HUMAN LICE

CROSS REFERENCE

This application claims priority of Provisional Application Ser. No. 60/091,658 filed Jul. 2, 1998.

BACKGROUND OF THE INVENTION

Infestation of the human body by lice is an increasingly prevalent social and health problem in many countries, including the United States. Lice are very small insects (about 2–3 mm in length). They deposit eggs either on a hair or fabric fiber and attach them firmly with a cementlike excretion. The eggs generally hatch in about six to ten days, depending on temperature. The empty shells remaining after the nymphs emerge from the eggs look like white grains of sand. These shells are called nits.

The Anoplura, or sucking lice, are parasites found on nearly all groups of mammals. Of the 15 recognized families of Anoplura, two families, Pediculidae and Pthiridae, have species found on humans. *Pediculus humanus* is the only species in the family Pediculidae that infests humans. It includes the head louse, *Pediculus humanus* capitis; and the body or clothing louse, *Pediculus humanus humanus*, sometimes called *Pediculus corporis*. The crab louse, *Pthirus pubis*, is a distinct species and is the only member of the family Pthiridae that infests humans. As used herein, the term "human lice or louse" includes a member of *Pediculus humanus* or *Pthirus pubis*.

Human lice are spread by crowding and common usage of clothing and combs. Initially, infestations result at most in irritation, but the irritation can lead to infection of the irritated area. There are at least three major diseases that are primarily transmitted by lice: epidemic typhus, trench fever and relapsing fever.

Although the human lice varieties are related, each of them has specific characteristics with regard to habitat and feeding. For example, head lice are small hard-shelled ectoparasites which cling to hair shafts while feeding, mating and laying eggs. The louse must remain on the head or it will die within a short period of time. Head lice proliferate at an incredible rate. A louse is ready to mate and reproduce within 10 hours after hatching. Under ideal conditions, a female louse may produce up to 300 eggs in its lifetime. Ideal conditions include an adequate food supply, environmental temperatures from about 28° C. to about 32° C., and relative humidity of about 70% to about 90%.

Poor hygienic and grooming habits are also known to contribute significantly to the spread of lice. Thus, lice infestations are most serious in geographical areas where the inhabitants have both substandard hygienic facilities and practices. Lice can be a problem, however, even when conditions are relatively sanitary.

The louse's hard chitinous exoskeleton serves as protection from external elements. Lice eggs (or ova) are similarly protected by a chitinous sheath surrounding the eggs and attached to the hair shaft. Although lice may be affected by the use of an insecticide, the eggs often remain resistant to attack. Thus, optimum treatment of a lice infestation includes both a pediculicide, which kills the adult lice, and an ovicide, which interrupts the development of the eggs.

Biologically active agents have been used for some time in attempts to control lice. For example, lindane (gammabenzene hexachloride), organophosphates (malathion), natural pyrethrins, and synthetic compounds known as pyrethroids (such as permethrin) have been used as pediculicides in lice treatment formulations. These agents however, have drawbacks. For example, lindane has a poor safety profile, and lice have developed resistance to it. Natural pyrethrin requires frequent follow-up treatments because it provides only short term residual action. Synthetic pyrethroids, although more effective against lice than natural pediculicides, are often more toxic to the subject being treated.

Spinosyns (also known as A83453 factors) are agricultural insecticides that have shown activity against 1) southern armyworm and other insects in the order Lepidoptera, 2) cotton aphid and other members of the order Homoptera, and 3) stable flies, blow flies and mosquitos, which are members of the insect order Diptera. (See U.S. Pat. No. 5,362,634, infra). Spinosyn A has an excellent human and animal safety and toxicological profile.

This invention provides formulations for controlling infestations of lice in a human comprising a spinosyn, or a physiologically acceptable derivative or salt thereof, and a physiologically acceptable carrier. It also provides methods of using these formulations to control human lice species. These formulations and methods control lice in a safer, more effective manner than previously known anti-lice formulations and methods.

SUMMARY OF THE INVENTION

This invention relates to formulations for controlling a lice infestation in a human comprising a spinosyn, or a physiologically acceptable derivative or salt thereof, and a physiologically acceptable carrier. The invention further relates to methods of controlling a lice infestation in a human comprising topically administering to the human an amount of a spinosyn, or a physiologically acceptable derivative/salt thereof, that controls the lice. The formulations and methods of this invention are safer and more effective than those presently available. A particular benefit of these formulations is their effectiveness against louse species that have become resistant to currently used products. Preferred formulations and methods of this invention are hair care formulations, such as shampoos, lotions and conditioners, and methods of using these hair care formulations for controlling a lice infestation in a human.

DETAILED DESCRIPTION OF THE INVENTION

This invention provides pediculicidal/ovicicdal (anti-lice) formulations for controlling a lice infestation in a human comprising as an active ingredient a spinosyn, or a physiologically acceptable derivative or salt thereof, and a physiologically acceptable carrier. Especially useful formulations of this invention are hair-care formulations. Especially useful hair-care formulations are shampoos.

This invention also provides methods for controlling a lice infestation in a human comprising topically administering a formulation comprising a spinosyn or a physiologically acceptable derivative or salt thereof, and a physiologically acceptable carrier. In another aspect this invention provides the use of a spinosyn, or a physiologically acceptable derivative or salt thereof, or a formulation containing either an spinosyn or derivative or salt thereof, for the manufacture of a medicament for controlling lice in a human.

The term "controlling a lice infestation" refers to treating an active lice infestation or preventing an infestation in a human who is likely to be exposed to a lice infestation.

Spinosyns are naturally derived fermentation products. They are macrolides produced by cultivation of *Saccha-* ropolyspora spinosa. The fermentation produces multifactors, including spinosyn A and spinosyn D (also called A83543A and A83543D). Spinosyn A and spinosyn D are the two spinosyns that are most active as insecticides. A product comprised mainly of these two spinosyns (approximately 85% A and 15% D) is available commercially from Dow Agrosciences under the name spinosad. The name "spinosad" comes from a contraction of the spinosyns "A" and "D".

Each spinosyn has a 12-membered macrocyclic ring that is part of an unusual tetracyclic ring system to which two different sugars are attached, the amino-sugar forosamine and the neutral sugar 2N,3N,4N-tri-O-methylrhamnose. This unique structure sets the spinosyns apart from other macrocyclic compounds.

Spinosyn A (A83543A) was the first spinosyn isolated and identified from the fermentation broth of *Saccharapolyspora spinosa*. Subsequent examination of the fermentation broth revealed that the parent strain of *S. spinosa* produced a number of spinosyns that have been labeled A to J (A83543A to J). Compared to spinosyn A, spinosyns B–J are characterized by differences in the substitution patterns on the amino group of the forosamine, at selected sites on the tetracyclic ring system and on 2N,3N,4N-tri-O-methylrhamnose. The strains of *S. spinosa* currently in use produce a mixture of spinosyns of which the primary components are spinosyn A (~85%) and spinosyn D (~15%). Additional spinosyns, lettered from K to W, have been identified from mutant strains of *S. spinosa*.

The term "spinosyn or a derivative thereof" as used herein refers to an individual spinosyn factor (A, B, C, D, E, F, G, H, J, K, L, M, N, O, P, Q, R, S, T, U, V, W or Y), an N-demethyl derivative of an individual spinosyn factor, or a combination thereof. For convenience, the term "spinosyn component" will also be used herein to mean an individual spinosyn, or a physiologically acceptable derivative or salt thereof, or a combination thereof.

Boeck et al. described spinosyns A–H and J (which they called A83543 factors A, B, C, D, E, F, G, H and J), and salts thereof, in U.S. Pat. No. 5,362,634 (issued Nov. 8, 1994); U.S. Pat. No. 5,496,932 (issued Mar. 5, 1996); and U.S. Pat. No. 5,571,901 (issued Nov. 5, 1996). Mynderse et al. described spinosyns L–N (which they called A83543 factors L, M and N), their N-demethyl derivatives, and salts thereof, in U.S. Pat. No. 5,202,242 (issued Apr. 13, 1993); and Turner et al. described spinosyns Q–T (which they called A83543 factors Q, R, S and T), their N-demethyl derivatives, and salts thereof, in U.S. Pat. No. 5,591,606 (issued Jan. 7, 1997) and U.S. Pat. No. 5,631,155 (issued May 29, 1997). These patents are incorporated herein by reference. Spinosyns K, O, P, U, V, W and Y are described, for example, by Carl V. DeAmicis, James E. Dripps, Chris J. Hatton and Laura I. Karr in American Chemical Society's Symposium Series: Phytochemicals for Pest Control, Chapter 11, "Physical and Biological Properties of Spinosyns: Novel Macrolide Pest-Control Agents from Fermentation", pages 146–154 (1997).

The spinosyns can react to form salts. Salts that are physiolocally acceptable are also useful in the formulations and methods of this invention. The salts are prepared using standard procedures for salt preparation. For example, spinosyn A can be neutralized with an appropriate acid to form an acid additional salt. The acid addition salts of spinosyns are particualrly useful. Representative suitable acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

In addition to the spinosyn component, the formulations of this invention may further include one or more other compounds that have activity against lice such as, for example, synthetic pyrethroids, natural pyrethins, and lindane. All ratios, percentages, and parts discussed herein are "by weight" unless otherwise specified.

Pediculicidal/Ovicidal Formulations

The anti-lice formulations of this invention may be formulated in a number of ways. Particularly useful formulations are shampoos, conditioners, and lotions. These formulations optionally also comprise one or more of the following: a) a surfactant; b) from about 1% to about 10% of a non-volatile silicone material; and/or c) from about 0.5% to about 5% of a suspending agent.

I. Shampoos

The shampoo formulations of this invention comprise a spinosyn, or a physiologically acceptable derivative or salt thereof, together with water, a surfactant, and an amide and may optionally comprise another anti-lice agent, a silicone compound, a suspending agent and other cosmetically acceptable components.

Human hair becomes soiled due to contact with the surrounding atmosphere and the build up of sebum secreted by the head. When the hair is soiled, it has a dirty feel and an unattractive appearance. The shampoo formulations of this invention both clean the hair and effectively control a lice infestation.

A. Spinosyn Component

When used in a shampoo formulation, the spinosyn component is present at a level of from about 0.1% to about 30%, preferably from about 1% to about 10%.

B. Surfactants

Surfactants suitable for use in these formulations can be any of a wide variety of synthetic anionic, amphoteric, zwitterionic and non-ionic surfactants. Surfactants are generally present in shampoo formulations at a level of from about 5% to about 30%, preferably from about 15% to about 25%.

Examples of synthetic anionic surfactants are the alkali metal salts of organic sulfuric reaction products having an alkyl radical containing from 8–22 carbon atoms and a sulfonic acid or sulfuric acid ester radical (included in the term alkyl is the alkyl portion of higher acyl radicals). Sodium, ammonium, potassium or triethanolamine alkyl sulfates are preferred, especially those obtained by sulfating the higher alcohols ($C_8$–$C_{18}$ carbon atoms); sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms; sodium alkyl glyceryl ether sulfonates; the reaction product of fatty acids having from 10 to 22 carbon atoms esterified with isethionic acid and neutralized with sodium hydroxide; and water soluble salts of condensation products of fatty acids with sarcosine.

Examples of zwitterionic surfactants are derivatives of aliphatic quaternary ammonium, phosphonium, and sulfonium compounds, in which the aliphatic radicals can be straight or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

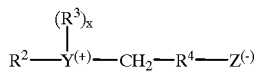

wherein $R^2$ contains an alkyl, alkenyl, or hydroxyalkyl radical of from about 8 to about 18 carbon atoms, from 0 to about 10 ethylene oxide moieties and from 0 to 1 glyceryl moiety; Y is a nitrogen, phosphorus, or sulfur atom; $R^3$ is an alkyl or monohydroxyalkyl group containing 1 to about 3 carbon atoms; x is 1 when Y is sulfur and 2 when Y is nitrogen or phosphorus; $R^4$ is alkylene or hydroxyalkylene of from 1 to about 4 carbon atoms, and Z is a carboxylate, sulfonate, sulfate, phosphonate, or phosphate radical.

Examples include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio] propane-1-phosphate;

3-(N,N-dimethyl-N-hexadecylammonio)propane-1-sulfonate;

3-(N,N-dimethyl-N-hexadecylammonio)-2-hydroxy-propane-1-sulfonate;

N,N-di(2-hydroxyethyl)-N-(2-hydroxydodecyl)ammonio] butane-1-carboxylate;

3-[S-ethyl-S-(3-dodecoxy-2-hydroxypropyl)sulfonio] propane-1-phosphate;

3-[P,P-dimethyl-P-dodecylphosphonio]-propane-1-phosphonate; and 5-(N,N-di(3-hydroxypropyl)-N-hexadecylammonio]-2-hydroxypentane-1-sulfate.

Other zwitterionic surfactants, such as betaines, are also useful in the formulations of this invention. Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine and lauryl bis-(2-hydroxypropyl)alpha-carboxyethyl betaine. The sulfobetaines may be represented by coco dimethyl sulfopropylbetaine, stearyl dimethyl sulfopropyl betaine, lauryl dimethyl sulfoethyl betaine, lauryl bis-(2-hydroxyethyl)sulfopropyl betaine, and the like. Amido betaines and amidosulfobetaines, wherein an RCONH $(CH_2)_3$ radical is attached to the nitrogen atom of the betaine, are also useful in the formulations of this invention.

Examples of amphoteric surfactants that can be used in the formulations of this invention are those which are derivatives of aliphatic secondary or tertiary amines in which the aliphatic radical is straight or branched and wherein one of the aliphatic substituents contains from about 8 to about 18 carbon atoms and one contains an anionic water solubilizing group, e.g., carboxy, sulfonate, sulfate, phosphate, or phosphonate. Examples of amphoteric surfactants are sodium 3-dodecylaminopropionate, sodium 3-dodecylaminopropane sulfonate, N-alkyltaurines such as the one prepared by reacting N-dodecylamine with sodium isethionate (see U.S. Pat. No. 2,658,072, Example 3), N-higher alkyl aspartic acids (see U.S. Pat. No. 2,438,091), and products sold under the trade name "Miranol" and described in U.S. Pat. No. 2,528,378.

Nonionic surfactants, which are preferably used in combination with an anionic, amphoteric or zwitterionic surfactant, are compounds produced by the condensation of alkylene oxide groups (hydrophilic in nature) with an organic hydrophobic compound, which may be aliphatic or alkyl aromatic in nature. Examples of nonionic surfactants include:

1. Polyethylene oxide condensates of alkyl phenols, e.g., the condensation products of alkyl phenols having an alkyl group containing from about 6 to 12 carbon atoms in either a straight or branched chain configuration, with ethylene oxide, the ethylene oxide being present in amounts equal to 10 to 60 moles of ethylene oxide per mole of alkyl phenol. The alkyl substituent in these compounds may be derived from polymerized propylene, diisobutylene, octane, or nonane, for example.

2. Condensates of ethylene oxide with a product of the reaction of propylene oxide and ethylene diamine products which may be varied in formulation depending upon the desired balance between the hydrophobic and hydrophilic elements. For example, compounds containing from about 40% to about 80% polyoxyethylene by weight and having a molecular weight of from about 5,000 to about 11,000 resulting from the reaction of ethylene oxide groups with a hydrophobic base comprising the reaction product of ethylene diamine and excess propylene oxide, and having a molecular weight on the order of 2,500 to 3,000, are satisfactory.

3. The condensation product of aliphatic alcohols having from 8 to 18 carbon atoms, in either straight or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

wherein $R_1$ contains an alkyl, alkenyl, or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxyethyl, or hydroxypropyl radicals. The arrow in the formula represents a semipolar bond. Examples of amine oxides suitable for use in these formulations include dimethyldodecylamine oxide, oleyldi(2-hydroxyethyl)amine oxide, dimethyloctylamine oxide, dimethyl-decylamine oxide, dimethyl-tetradecylamine oxide, 3,6,9-trioxaheptadecyldiethylamine oxide, di(2-hydroxyethyl)tetradecylamine oxide, 2-dodecoxyethyldimethylamine oxide, 3-dodecoxy-2-hydroxypropyldi(3-hydroxypropyl)amine oxide, and dimethylhexadecylamine oxide.

5. Long chain tertiary phosphine oxides of the following general formula:

wherein R contains an alkyl, alkenyl or monohydroxy-alkyl radical of from about 8 to 18 carbon atoms, from 0 to about 10 ethylene oxide moieties and from 0 to 1 glyceryl moiety, and R' and R" are each alkyl or monohydroxyalkyl groups containing from 1 to 3 carbon atoms. The arrow in the formula represents a semipolar bond.

Examples of suitable phosphine oxides include: dodecyldimethyl-phosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl)phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxyalkyl radical of 1 to 3 carbon atoms (usually methyl) and one long hydrophobic chain which contains alkyl, alkenyl, hydroxyalkyl, or keto alkyl radicals containing form about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, and 3-hydroxy-4-dodecoxybutyl methyl sulfoxide.

Many additional nonsoap surfactants are described in *McCutcheon's Detergents and Emulsifiers*, 1998 Annual, published by M.C. Publishing Company, Inc.; McCutcheon Division, 175 Rock Rd., Glen Rock, N.J., 07425, U.S.A.

Anionic surfactants, particularly the alkyl sulfates, the ethoxylated alkyl sulfates and mixtures thereof, as well as the amido betaines, are preferred for use in the shampoo formulations of this invention.

C. Amides

Amides enhance the lathering of the formulations by emulsifying the shampoo components and the active component(s). The amides used in the present formulations can be any of the alkanolamides of fatty acids known for use in shampoos. These are generally mono- and diethanolamides of fatty acids having from about 8 to about 14 carbon atoms. Other suitable amides are those having multiple ethos, groups such as PEG-3 lauramide.

In the shampoo formulations, the amide is generally present at a level of about 1% to about 7%, preferably from about 2% to about 5%, of the formulation. Prefered amides are coconut monoethanolamide, coconut diethanolamide, and mixtures thereof.

D. Water

The shampoo formulations of this invention also contain water. Water is typically present in the shampoos at levels of from about 50% to about 80%, preferably from about 60% to about 75%. After adding water, the relative viscosity of the formulation is generally in the range of from about 4,000 centipoise (cp) to about 25,000 cp, preferably from about 4,000 cp to about 12,000 cp, most preferably from about 4,000 cp to about 5,500 cp, measured at 1 RPM at 26.7° for 3 minutes using a Wells-Brookfield viscometer Model DV-CP-2 DVII, Model Cone CP-41. Viscosity modifiers and hydrotropes may be included to bring the formulation's viscosity within these ranges.

E. Optional Components

1. Silicone compounds may be incorporated into the shampoo formulations to condition the hair and facilitate removal of the dead lice, their eggs and nits. Non-volatile silicone materials are used at levels from about 1% to about 10% of the formulations. Examples of useful silicone compounds are disclosed in U.S. Pat. No. 5,292,504, Cardin et al., issued Mar. 8, 1994, incorporated herein by reference.

Non-volatile silicone-containing compounds are preferred and are used at levels of from about 0.1% to about 10%, preferably from about 0.25% to about 3%, by weight of the formulation. Examples of non-volatile silicones are polyalkyl siloxanes, poly alkylaryl siloxanes, polyether siloxane copolymers and mixtures thereof.

Useful polyalkyl siloxanes include, for example, polydimethyl siloxanes (PDMS) with viscosities ranging from about 5 to 15,000,000 cp at 25°. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, Jul. 20, 1970.

Useful polyalkylaryl siloxanes include polymethylphenyl siloxanes having viscosities of from about 5 to about 15,000,000 cp at 25°. These siloxanes are available, for example, from the General Electric Company as SF 1075 methyl phenyl fluid or from Dow Corning as 556 Cosmetic Grade Fluid.

Useful polyether siloxane copolymers include polypropylene oxide modified polydimethylsiloxanes (available, for example, from Dow Corning as DC-1248), ethylene oxide or mixtures of ethylene oxide and propylene oxide. Water insoluble ones are most useful.

The siloxanes are able to condition the hair due to their ability to lubricate the hair, providing wet and dry combing benefits. Viscous, higher molecular weight siloxanes provide the best conditioning benefits and are, therefore, preferred. Fluids and gums of the siloxane polymers are most desirable. Siloxane polymer gums are rigid as opposed to a liquid or fluid, with high mass molecular weights of from about 200,000 to about 1,000,000 as viscosities from about 100,000 cp to about 150,000,000 cp at 25° C. Such gums are discussed in U.S. Pat. No. 5,292,504 (supra).

2. The shampoo formulations may incorporate suspending agents to improve long term stability. Useful suspending agents include fatty amphiphilic crystalline materials having needle-like or platelet structures, polymeric materials, clays, fumed metal oxides, and mixtures thereof. These agents are known in the art (see U.S. Pat. No. 5,292,504).

Suitable crystalline amphiphilic materials are those that have needle or platelet-type structures. Such comounds include long chain ($C_{16}$–$C_{22}$) acyl derivatives, such as ethylene glycol esters of fatty acids (e.g., ethylene glycol disterate); long chain ($C_{16}$–$C_{22}$) alkanol amides of fatty acids, such as stearamide MEA, stearyl stearate, and distearyl dithiopropionate; and mixtures thereof.

Polymeric materials that are useful as suspending agents include cross-linked polyacyclic acids (such as the Carbopol series, available from the B.F. Goodrich Chemical Company), guar gum and its derivatives, xanthan gum, cross linked copolymers of ethylene/maleic anhydrides, and mixtures thereof.

Clays and fumed metal oxides are also effective suspending agents. Examples include magnesium aluminum silicates (such as the Veegum series, available from R.T. Vanderbilt Company, Inc.), sodium aluminum silicates (such as the Laponite series, available from Laponite United States), fumed silica, fumed alumina, fumed titania and mixtures thereof.

In the shampoo formulations of this invention suspending agents are generally present in amounts of from about 0.5% to about 5%, preferably from 0.5% to about 3%. The long chain acyl derivatives such as ethylene glycol esters of fatty acids are preferred. Most preferred is ethylene glycol distearate.

3. The shampoo formulations can also contain a variety of other components suitable for rendering the formulations more cosmetically acceptable. Such optional ingredients are known in the art and include, e.g., preservatives, such as methyl para ben, propyl para ben, methylisothiazolinone and imidazolidinyl urea; thickeners and viscosity modifiers, such as amine oxides, block polymers of ethylene oxide and propylene oxide (such as Pluronic F88 offered by BASF Wyandotte), fatty alcohols (such as cetearyl alcohol), sodium choloride, ammonium chloride, sodium sulfate, polyvinyl alcohol, propylene glycol, and ethyl alcohol; hydrotropes, such as xylene sulfonate; pH adjusting agents, such as citric acid, succinic acid, phosphoric acid, sodium hydroxide, and sodium carbonate; perfumes, dyes, quaternary ammonium compounds, such as Polyquaternium 41, sequestering agents, such as disodium ethylenediamine tetraacetate; and pearlescing agents, such as distearic acid ester of ethylene glycol, stearic acid and palmitic acid diesters of polyethylene glycol, and stearic acid monoethanolaminde. Generally, these optional components are used individually at a level of from about 0.1% to about 10% of the formulation.

The shampoo formulations of this invention are used in a conventional manner for cleaning hair. From about 10 g to about 30 g of a formulation is applied to wet hair and worked through both hair and scalp. The formulation is left on the hair and scalp for approximately 6–10 minutes and then is removed by rinsing. This process is repeated until the hair is clean.

A useful pediculicidal shampoo of this invention comprises:

(a) from about 0.1% to about 2.5% of a spinosyn, or a physiologically acceptable derivative or salt thereof;

(b) from about 5% to about 30% of a synthetic surfactant;

(c) from about 1% to about 7% of an amide; and (d) water.

II. Hair Conditioner Formulations

The hair conditioning formulations of this invention comprise a spinosyn component and a conditioner and may optionally comprise another anti-lice agent, such as permethrin or lindane. These conditioner formulations may also be used effectively to treat a lice infestation.

Hair conditioners are products that improve the appearance, feel and manageability of hair. Conditioners are particularly important when the hair has been damaged by treatments such as permanent waving, dyeing, teasing, and bleaching, or by atmospheric conditions, such as sunlight, that cause photo-catalyzed oxidation. These factors may cause hair to have poor texture, making it difficult to manage and comb, whether wet or dry.

Conditioning products are well known and include "rinse-type" products, which are rinsed off shortly after being applied to clean hair, and "deep conditioners" which remain on the hair for extended periods of time.

A. Spinosyn Component

When used in hair conditioner formulations, the spinosyn component is present at a level of from about 0.1% to about 30%, preferably from about 1% to about 10%.

B. Conditioners

One group of conditioners useful in the hair conditioner formulations of this invention are long chain quaternary ammonium compounds combined with lipid materials, such as fatty alcohols (see U.S. Pat. No. 3,155,591, Hilfer, issued Nov. 3, 1964, and U.S. Pat. No. 4,269,824, Villamarin, et al., issued May 26, 1981). Another group of conditioners are lipids and quaternary ammonium compounds. These conditioners are used to form gel-type conditioner products having good in-use cosmetic and Theological characteristics. These types of gel-type formulations are generally described in the following documents: Barry "The Self Bodying Action of the Mixed Emulsifer Sodium Docecyl Sulfate/ Cetyl Alcohol", *J. of Colloid and Interface Science,* 28, 82–91 (1968); Barry et al., "The Self-Bodying Action of Alkyltrimethylammonium Bromides/Cetostearyl Alcohol Mixed Emulsifiers; Influence of Quarternary Chain Length", *J. of Colloid and Interface Science,* 35, 689–708 (1971); and Barry et al., "Rheology of Systems Containing Cetomacrogo/1000-(cetostearyl alcohol), I. Self-Bodying Action", *J. of Colloid and Interface Science,* 38, 616–625 (1972).

1. Lipid Materials

The lipid materials used in these conditioners are present at a level of from about 0.5% to about 3%. These lipids are essentially water-insoluble, and contain hydrophobic and hydrophilic moieties. They include natural and synthetically-derived fatty materials selected from acids, acid derivatives, alcohols, esters, ethers, ketones, amides, and mixtures thereof, having alkyl chain lengths from about 12 to about 22 carbon atoms, preferably from 16 to 18 carbon atoms in length. Fatty alcohols and fatty esters are preferred.

Useful fatty alcohols are known (see, for example, U.S. Pat. No. 3,155,591, supra; U.S. Pat. No. 4,165,369 (Watanabe et al., issued May 26, 1981); British Patent Specification 1,532,585, published Nov. 15, 1978; Fukushima et al., "The Effect of Cetostearyl Alcohol in Cosmetic Emulsions", *Cosmetics & Toiletries,* 98, 89–102 (1983); and Hunting, *Encyclopedia of Conditioning Rinse Ingredients,* at 204 (1987). Fatty alcohols are $C_{12}$–$C_{16}$ alcohols selected from cetearyl alcohol, cetyl alcohol, isostearyl alcohol, lanolin alcohol, lauryl alcohol, oleyl alcohol, stearyl alcohol, and mixtures thereof. Preferred are cetyl alcohol, stearyl alcohol, and mixtures thereof. A particularly preferred fatty alcohol is comprised of a mixture of cetyl alcohol and stearyl alcohol containing from about 55% to about 65% (by weight of mixture) of cetyl alcohol.

Useful fatty esters are also known (see Kaufman, et al., U.S. Pat. No. 3,341,465, issued Sep. 12, 1967). Fatty esters are fatty acids in which the active hydrogen has been replaced by the alkyl group of a monohydric alcohol. The monohydric alcohols are fatty alcohols as described, supra. The fatty esters useful in these conditioner formulations include cetyl lactate, cetyl octanoate, cetyl palmitate, cetyl stearate, glyceryl monostearate, glyceryl laurate, glyceryl myristate, glyceryl oleate, glyceryl stearate, glyceryl monoacetate, and mixtures thereof. Cetyl palmitate and glycerol monostearate, or mixtures thereof, are preferred.

2. Surfactants

Cationic surfactants may be used in these conditioning formulations, either singly or in combination, generally at a level of from about 0.1% to about 5% of the final formulation. These surfactants contain amino or quaternary ammonium hydrophilic moieties that are positively charged when dissolved in the aqueous formulations of this invention. These cationic surfactants are known in the art (see *McCutcheon's Detergents & Emulsifiers,* supra; Schwartz et al., *Surface Active Agents, Their Chemistry and Technology,* New York: Interscience Publishers, 1949; U.S. Pat. No.

3,155,591, supra; U.S. Pat. No. 3,929,678 (Laughlin et al., issued Dec. 30, 1975); U.S. Pat. No. 3,959,461 (Bailey et al., issued May 25, 1976); and U.S. Pat. No. 4,387,090 (Bolich, Jr., issued Jun. 7, 1983).

Useful quaternary ammonium cationic surfactant materials are those of the general formula:

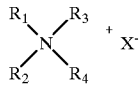

wherein $R_1$ is hydrogen, an aliphatic group of from 1 to 22 carbon atoms, or an aromatic, aryl or alkylaryl group having from 12 to 22 carbon atoms; $R_2$ is an aliphatic group having from 1 to 22 atoms; $R_3$ and $R_4$ are each alkyl groups having from 1 to 3 carbon atoms, and X is an anion selected from halogen, acetate, phosphate, nitrate and alkyl sulfate radicals. The aliphatic groups may contain ether linkages, and other groups such as amido groups, in addition to carbon and hydrogen atoms.

Other useful quaternary ammonium salts have the formula:

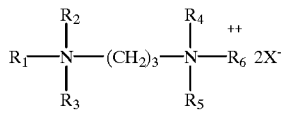

wherein at least one, but no more than 3, of the R groups is an aliphatic group having from 16 to 22 carbon atoms, and the remaining R groups are selected from hydrogen and alkyl groups having from 1 to 4 carbon atoms, and X is an ion selected from halogen, acetate, phosphate, nitrate and alkyl sulfate radicals Tallow propane diammonium dichloride is an example of this type of quaternary ammonium salt.

Quaternary ammonium salts useful herein also include dialkyldimethylammonium chlorides wherein the allkyl groups have from 12 to 22 carbon atoms. These alkyl groups may be derived from long-chain fatty acids, such as hydrogenated tallow fatty acid. Tallow fatty acid gives rise to quaternary compounds wherein $R_1$ and $R_2$ predominantly have from 16 to 18 carbon atoms. Examples include ditallow dimethyl ammonium chloride, ditallow dimethyl ammonium methyl sulfate, dihexadecyl dimethyl ammonium chloride, di(hydrogenated tallow)dimethyl ammonium chloride, dioctadecyl dimethyl ammonium chloride, dieicosyl dimethyl ammonium chloride, didocosyl dimethyl ammonium chloride,. di(hydrogenated tallow)dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl)dimethyl ammonium chloride, and stearyl dimethyl benzyl ammonium chloride. Preferred quaternary ammonium salts useful herein include ditallow dimethyl ammonium chloride, dicetyl dimethyl ammonium chloride, stearyl dimethyl benzyl ammonium chloride, cetyl trimethyl ammonium chloride, tricetyl methyl ammonium chloride, and mixtures thereof. Di(hydrogenated tallow) dimethyl ammonium chloride (Quaternium-18) is a particularly preferred quaternary ammonium salt, and is available from the Sherex Chemical Company, Inc. as Adogen 442 and Adogen 442-100P.

Salts of primary, secondary and tertiary fatty amines may also be used as a cationic surfactant. The alkyl groups of such amines preferably have from 12 to 22 carbon atoms, and may be substituted or unsubstituted. Secondary and tertiary amines are preferred; and tertiary amines are particularly preferred. Examples of useful amines include stearamido propyl dimethyl amine, diethyl amino ethyl stearamine, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Examples include stearylamine hydrochloride, soyamine chloride, stearylamine formate, N-tallowpropane diamine dichloride and stearamidopropyl dimethylamine citrate. Useful cationic amine surfactants are also disclosed in U.S. Pat. No. 4,275,055 (Nachtigal et al., issued Jun. 23, 1982).

3. Water

Water is an essential ingredient in the conditioner formulations. Water is added as the last step in preparing the conditioner, using an amount sufficient to bring (q.s.) the mixture to 100%.

4. Optional Ingredients

Silicone conditioning agents may be used for their cosmetic and rheological charcteristics. Silicone oils and silicone polymers are well known conditioning agents. For example, volatile silicones, organosilicone polymers in water-alcohol mixtures, and volatile silicone fluids are disclosed in U.S. Pat. No. 5,292,502, supra.

The formulation may include one or more silicones disclosed for use in the shampoo formulations supra. These silicones include volatile and non-volatile polyalkyl siloxanes, polyalkylaryl siloxanes, and mixtures thereof. They may be used at levels from about 0.2% to about 5% of the final formulation.

As with shampoos, the higher viscosity silicone gums of the siloxanes disclosed supra are preferred. These gums are rigid, as opposed to a fluid, with high molecular weights of from about 200,000 to aobut 1,000,000 and viscosities from about 100,000 cp to about 150,000,000 cp at 25°. Most preferred are the polydimethylsiloxane gums.

Often a significant amount of the lipid material in the conditioner is deposited on the hair, leaving it greasy. The conditioner formulations may, therefore, incorporate silicone copolyols to provide optimum conditioning benefits with the anti-lice treatment. See European Patent Application 155,806, published Sep. 25. 1985.

The silicone copolyols are polyalkylene oxide modified dimethylpolysiloxanes, herein referred to as a "dimethicone copolyols" that act as an emulsifier and reduce the deposition of the vehicle materials (lipid materials and/or cationic surfactants) on the hair. Useful dimethicome copolyols are also disclosed in U.S. Pat. No. 5,292,504, supra.

The silicone copolyol is generally present at a level of from about 0.1% to about 10%, preferably from about 0.1% to about 2%, of the final formulation.

Dimethicone copolyols are preferred for this use. Dow Corning 190 Silicone Surfactant is a preferred dimethicone copolyol.

The formulations may also contain components that modify the physical and performance characteristics of the conditioning product. Such components include additional surfactants, salts, buffers, thickeners, solvents, opacifiers, pearlescent aids, preservatives, fragrance, colorants, dyes, pigments, chelators, sunscreens, vitamins, and medicinal agents. Examples of these types of components are disclosed in U.S. Pat. No. 4,387,090 (Bolich, Jr., issued Jun. 7, 1983).

The formulations may also contain optional surfactant materials at levels such that the total level of surfactant present in the formulation (including the cationic surfactant vehicle material, described supra) is from about 0.05% to about 5%. These optional surfactant materials may be anionic, nonionic or amphoteric. Examples are ceteareth-20, steareth-20, sorbitan monoesters, sodium tallow alkylsulfate, and tallow betaine. Optional surfactant materials are described in McCutcheon's *Detergents & Emulsifiers*, supra; Schwarts et al., supra; and U.S. Pat. No. 3,929,678 supra.

Preferred optional surfactant materials are nonionic. Such surfactants are most commonly produced by the condensation of an alkylene oxide (hydrophilic in nature) with an organic hydrophobic compound that is usually aliphatic or alkyl aromatic in nature. The length of the hydrophilic or polyalkylene moiety that is condensed with any particular hydrophobic compound can be adjusted to yield a water-soluble compound having the desired degree of balance between hydrophilic and hydrophobic elements. Such nonionic surfactants include polyethylene oxide condensates of alkyl phenols, condensation products of aliphatic alcohols with ethylene oxide, condensation products of ethylene oxide with a hydrophobic base formed by condensation of propylene oxide with propylene glycol, and condensation products of ethylene oxide with the product resulting from the reaction of propylene oxide and ethylene diamine. Another variety of nonionic surfactant is a non-polar non-ionic surfactant, typified by the amine oxide surfactants. Preferred nonionic surfactants include ceteareth-20, steareth-20 and ceteth-2.

Salts and buffers may also be added in order to modify the product rheology. For example, salts such as potassium chloride, ammonium chloride, and sodium chloride, may be added at levels of form about 0.001% to about 1%. Buffers, such as citrate or phosphate buffers, may also be added. The present formulations as finally formulated preferably have a pH of from about 3 to about 10, most preferably from about 3 to about 7.

Additional conditioning components may also be incorporated into the formulations. For example, proteins may be added at levels of from about 0.1% to about 10%. Cationic proteins may also serve as surfactant vehicle materials.

Thickening agents are preferred optional components. Such thickeners include nonionic thickening agents that are incorporated at levels of from about 0.1% to about 8%. Such agents are polymers that exhibit viscosities exceeding about 20,000 cp at low shear (about $10^{-2}$ sec$^{-1}$). Examples are polyoxyethylene, guar gum, methylcellulose, methyl hydroxypropyl cellulose, polypropyl cellulose, polypropyl hydroxyethyl cellulose, hydroxyethyl cellulose, starches and starch derivatives, and mixtures thereof. Nonionic thickening agents are disclosed in U.S. Pat. No. 4,387,090 (Bolich et al., issued Jun. 7, 1983).

The thickening agents are used to bring the viscosity of the formulation from about 10,625 cp to about 14,375 cp (as measured with a Wells-Brookfield viscometer, Model RVT DV-CP-2, DV-11, Model Cone CP-52, using ½ mL at 1 rpm at 26.7°. for 1 minute).

The hair conditioning formulations of this invention are generally used on the hair after all shampoo has been removed by rinsing with water.

This invention also provides a method for treating human hair to kill and facilitate removal of lice and their eggs, comprising the steps of:

(a) applying from about 10 grams to about 30 grams of a formulation of this invention to the wet hair;
(b) working the formulation through the hair and scalp;
(c) leaving the formulation on the hair and scalp for about 6–10 minutes; and
(d) removing the formulation from the hair by rinsing with water.

III. Lotions

Anti-lice lotions comprising a spinosyn, or a physiologically acceptable derivative or salt thereof, and a lotion carrier are another aspect of this invention. These lotions can be applied directly onto the hair in liquid form or in spray form. They are formulated to be applied to the hair for a period of time and not immediately removed by rinsing with water.

A. Spinosyn Component

When used in a lotion formulation of this invention, the spinosyn component is generally present at a level of from about 0.1% to about 30%, preferably from about 1% to about 10%.

B. Liquid Vehicle

In addition to the spinosyn component, the lotion formulations of this invention comprise a liquid vehicle such as alcohol, water or a mixture thereof, to assist in delivery of the spinosyn component to the hair. Suitable alcohols are monohydric alcohols such as methanol, ethanol, isopropanol, or mixtures thereof. Since alcohols can have a deleterious effect upon the stability of the formulations, water alone is most preferred as the vehicle. The vehicle is added in an amount necessary to q.s. the formulation to 100%.

C. Optional Components

The lotion formulations of this invention may include optional components to provide benefits to the hair in addition to the anti-lice activity. Optional components include: preservatives and antimicrobials, such as DMDM hydantoin and tetrasodium EDTA; pH balancing agents, such as sodium citrate and citric acid; emulsifiers, such as PEG-60 castor oil; and thickeners and viscosity modifiers, such as polyvinylpyrrolidone. When included, such components generally are used individually at a level from about 0.01% to about 10%.

Conditioning agents may be included to facilitate the removal of dead lice and eggs from the hair and to provide good wet and dry combing. The same types of conditioning agents described in the conditioning formulations supra may be used in the lotions; these include quaternary ammonium salts, fatty amines and mixtures thereof. Conditioning agents are used at levels from about 0.1% to about 1%, preferably from about 0.4% to about 0.6%.

Preferred conditioning agents are quaternary ammonium salts. Preferred quaternary ammonium salts include dialkyldimethylammonium chlorides, wherein the alkyl groups have from 12 to 22 carbon atoms. These alkyl groups may be derived from long-chain fatty acids, such as hydrogenated tallow fatty acid. Tallow fatty acid gives rise to quaternary compounds wherein $R_1$ and $R_2$ predominantly have from 16 to 18 carbon atoms. Examples of quaternary ammonium salts useful in the lotion formulations include di(hydrogenated)tallow dimethyl ammonium chloride, dicetyl dimethyl ammonium chloride, tricetyl methyl ammonium chloride, cetyl trimethyl ammonium chloride, stearyl dimethyl benzyl ammonium chloride, and mixtures thereof. Most preferred is dicetyl dimethyl ammonium chloride.

Alcohol synergizers may also be added to the lotion formulations to enhance their anti-lice activity. The alcohols used in the lotion formulations are selected from phenyl $C_2$–$C_6$ alkanols, phenyl $C_2$–$C_6$ diols, $C_2$–$C_8$ alkylene diols, and mixtures thereof. These synergizers may be included at levels from about 0.25% to about 10%, wherein the level of phenyl alkanols, phenyl diols, and mixtures thereof, does not exceed 5% of the formulation. Preferably, the level is about 0.5% to about 5% of the formulation, most preferably from about 2% to about 4%. A preferred synergizer is hexylene glycol.

The lotion formulations of this invention are applied directly to the hair. The amount of lotion used is generally from about 10 mL to about 50 mL. The lotion is worked through the hair and left on the hair for about 10 minutes, preferably about 30 minutes. The hair is then cleansed, generally with a shampoo, before rinsing with water.

The following examples illustrate the formulations of this invention:

EXAMPLE 1

A lotion formulation is prepared as follows:

| Component | Weight (%) |
|---|---|
| Polyvinylpyrrolidone | 0.50 |
| DMDM hydantoin | 0.20 |
| Tetrasodium EDTA | 0.13 |
| Citric acid | 0.05 |
| PEG-60 castor oil | 0.50 |
| Hexylene glycol | 4.00 |
| Dicetyl dimethyl ammonium chloride | 0.38 |
| Spinosyn A | 0.50 |
| Water q.s. to | 100.00 |

Add the spinosyn to a tank containing a mixture of PEG-60 castor oil, hexylene glycol, propylene glycol and dicetyl dimethyl ammonium chloride at between 35° to 38°. In a second tank, mix polyvinyl pyrrolidone, DMDM hydantoin, tetrasodium EDTA and citric acid and bring the mixture to a temperature between 35° to 38°. Add the contents of the first tank to the second tank and mix until uniform. Cool the mixture to about 27°, and empty into storage drums.

EXAMPLE 2

A lotion formulation is prepared using the procedure described in Example 1, but with the following formula.

| Component | Weight (%) |
|---|---|
| Polyvinylpyrrolidone | 0.50 |
| DMDM hydantoin | 0.20 |
| Tetrasodium EDTA | 0.13 |
| Citric acid | 0.05 |
| PEG-60 castor oil | 0.50 |
| Hexylene glycol | 2.00 |
| Propylene glycol | 2.00 |
| Dicetyl dimethyl ammonium chloride | 0.38 |
| Spinosad | 0.25 |
| Water q.s. to | 100.00 |

EXAMPLE 3

A lotion formulation is prepared by the procedure described in Example 1, but with the following formula:

| Component | Weight (%) |
|---|---|
| Polyvinylpyrrolidone | 0.50 |
| DMDM hydantoin | 0.20 |
| Tetrasodium EDTA | 0.13 |
| Citric acid | 0.05 |
| Isopropanol | 1.00 |
| PEG-60 castor oil | 0.50 |
| Hexylene glycol | 4.00 |
| Dicetyl dimethyl ammonium chloride | 0.60 |
| Spinosyn component | 0.10 |
| Water q.s. to | 100.00 |

To control a lice infestation, the lotion formulations of Examples 1–3 are applied to the hair and left on for at least ½ hour before being removed by shampooing or rinsing.

EXAMPLE 4

A shampoo formulation is prepared as follows:

| Component | Weight (%) |
|---|---|
| Ammonium laureth sulfate | 10.40 |
| Ammonium lauryl sulfate | 9.50 |
| Coconut monoethanolamide | 4.00 |
| Ethylene glycol distearate | 3.00 |
| DMDM hydantoin | 0.20 |
| Monosodium phosphate | 0.10 |
| Disodium phosphate | 0.25 |
| Citric acid | 0.07 |
| Ammonium xylenesulfonate | 1.58 |
| Spinosyn A | 0.50 |
| Water q.s. to | 100.00 |

Add the ammonium lauryl sulfate to a tank and heat to between about 66° to about 69°. While maintaining this temperature, add an aqueous solution of mono-sodium phosphate and then an aqueous solution of disodium phosphate. Upon reaching 69°, add the ammonium xylenesulfonate to the mixture and heat to from about; 74° to 77°; add the cononut monoethanolamide, mixing until well dispersed, the ethylene glycol distearate and about 4.5% of the water. Continue mixing until homogeneous and cool mixture to about 41°. Pump the mixture into a second tank and add the ammonium laureth sulfate, DMDM hydantoin, and aqueous solution of citric acid. Add the a spinosyn to the second tank and q.s. to 100% with water. Mix thoroughly, cool to about 27°, and pump the mixture into storage drums.

EXAMPLE 5

A shampoo formulation is prepared as follows:

| Component | Weight |
|---|---|
| Ammonium laureth sulfate | 14.15 |
| Ammonium lauryl sulfate | 3.14 |
| Coconut monoethanolamide | 3.00 |
| Ethylene glycol distearate | 3.00 |
| Silicone gum[1] | 0.50 |
| Dimethicone fluid (350 cp) | 0.50 |
| Tricetyl methyl ammonium chloride | 0.29 |
| Cetyl alcohol | 0.42 |
| Stearyl alcohol | 0.18 |
| DMDM hydantoin | 0.20 |
| Sodium chloride | 0.90 |

-continued

| Component | Weight |
| --- | --- |
| Ammonium chloride | 0.05 |
| Ammonium xylenesulfonate | 1.25 |
| Spinosad | 0.40 |
| Water q.s. to | 100.00 |

[1]Silicone gum available from The General Electric Co. as SE-30 or SE-76 Gum.

Add approximately 0.5% of the ammonium laureth sulfate and the dimethicone to a container, and mix for approximately 30 minutes. Add approximately 2% ammonium laureth sulfate to a processing tank and heat to 68° to 71°. Add about 0.12% stearyl alcohol, about 0.06% of cetyl alcohol, and the contents of the first container to the processing tank. Mix until uniform, maintaining the mixture between 68° and 71°. To a second processing tank, add ammonium lauryl sulfate and heat to about 71°. While maintaining this temperature, add 0.05% ammonium chloride, about 18% water, ammonium xylenesulfonate and the remainder of the stearyl and cetyl alcohols. Add coconut monoethanolamide, tricetyl methyl ammonium chloride, ethylene glycol distearate, approximately half the DMDM hydantoin and the contents of the first tank to the second tank while maintaining a temperature of about 77°. Mix until homogenous and then cool to about 41°. Pump to a third tank and add the remainder of the ammonium laureth sulfate, DMDM hydantoin, and sodium chloride. Add the spinosyn to the mixture and q.s. to 100% with water. Mix thoroughly, cool to about 27°, and pump the mixture into storage drums.

EXAMPLE 6

A shampoo formulation is prepared as follows:

| Component | Weight % |
| --- | --- |
| Ammonium laureth sulfate | 12.81 |
| Ammonium lauryl sulfate | 9.10 |
| Coconut monoethanolamide | 2.30 |
| Isostearyl ethylmidonium ethosulfate | 1.25 |
| DMDM hydantoin | 0.20 |
| Monosodium phosphate | 0.50 |
| Disodium phosphate | 0.38 |
| Sodium chloride | 0.04 |
| Citric acid | 0.10 |
| Ammonium xylenesulfonate | 1.35 |
| Spinosyn component | 0.56 |
| Water q.s. to | 100.00 |

Add about 6.5% of the water and the ammonium laureth sulfate to a mixing tank and heat the mixture to about 35°. While maintaining this temperature, add the following components individually in sequence, mixing so that each component is well mixed into the batch: ammonium lauryl sulfate, ammonium xylenesulfonate, monosodium phosphate, disodium phosphate, DMDM hydantoin, sodium chloride, a solution of citric acid and water, a solution of coconut diethanolamide and isostearyl ethylmidonium ethosulfate. Add the spinosyn to the mixture, and q.s. to 100% with water. Mix thoroughly, cool to about 27°, and pump the mixture into storage drums.

EXAMPLE 7

A conditioner formulation of this invention is prepared as follows:

| Component | Weight % |
| --- | --- |
| Cetyl alcohol | 1.00 |
| Stearyl alcohol | 0.72 |
| DMDM hydantoin | 0.20 |
| Hydroxyethyl cellulose | 0.50 |
| Quaternium-18 | 0.85 |
| Ceteareth-20 | 0.35 |
| Stearalkonium chloride | 0.85 |
| Glyceryl monostearate | 0.25 |
| Citric acid | 0.08 |
| Silicone gum[1] | 0.30 |
| Cyclomethicone fluid | 1.70 |
| Spinosyn A | 1.00 |
| Water q.s. to | 100.00 |

[1]Silicone gum available from The General Electric Co. as SE-30 or SE-76 Gum.

Combine all components, except the DMDM hydantoin, citric acid, silicone gum, cyclomethicone, and a spinosyn, in a processing tank and heat the mixture to about 88°. After the solution is thoroughly mixed, cool it to approximately 48°. In a separate tank, premix the silicone gum and cyclomethicone, with heat and agitation to form a gum solution. Add the spinosyn to this mixture. Add the gum solution and all the remaining components, and q.s. with water. Mix thoroughly, cool to about 27°, and pump the mixture into storage drums.

EXAMPLE 8

A conditioner formulation is prepared by the procedure described in Example 7, but using the following formula:

| Component | Weight % |
| --- | --- |
| Cetyl alcohol | 1.00 |
| Stearyl alcohol | 0.72 |
| DMDM hydantoin | 0.20 |
| Hydroxyethyl cellulose | 0.50 |
| Quaternium-18 | 0.85 |
| Ceteareth-20 | 0.35 |
| Stearamidopropyldimethyl amine (SAPDMA) | 0.50 |
| Glyceryl monostearate | 0.25 |
| Citric acid | 0.08 |
| Sodium Citrate | 0.05 |
| Stearoxydimethicone | 0.10 |
| Silicone gum[1] | 0.05 |
| Cyclomethicone fluid | 1.70 |
| Spinosyn component | 1.00 |
| Water q.s. to | 100.00 |

[1]Silicone gum available from the General Electric Co. as SE-30 or SE-76 Gum.

This conditioner anti-lice product is made in a manner similar to that described in Example 7.

EXAMPLE 9

Efficacy of Shampoo Formulations

Shampoo formulations containing various concentrations of spinosad were used in this study. The formulations were prepared by wet milling for 30 minutes enough technical grade spinosad into a commercially available shampoo (Johnson's® Baby Shampoo, Moisturizing Formula with Honey and Vitamin E, Johnson & Johnson Consumer Products, Inc.) to form a 10% stock spinosad/shampoo mixture. This mixture was diluted with additional shampoo to prepare the following spinosad concentrations: 10% (used as originally prepared), 1%, 0.1% and 0.01% spinosad/shampoo (w/w).

The four concentrations of spinosad in shampoo and a control of tap water were tested against adult human body lice (*Pediculus humanus humanus*) according to a standard test, ASTM Standard E 938-83 (Reapproved 1988), that is available from the American Society for Testing and Materials, 100 Barr Harbor Drive, West Conshohocken, Pa. USA [http://www.astm.org/]. In this test, 25 adult lice were immersed in each of the four shampoo concentrations for 10 minutes, then washed in water for 1 minute and rinsed in water for another minute. In the control group, 25 adult lice (*Pediculus humanus humanus*) were immersed in tap water for 10 minutes, then washed in water for 1 minute, and rinsed in water for another minute. A total of 5 trials were performed.

After one hour, the lice were examined to determine the knockdown number. "Knockdown" was measured as the rather quick (within a matter of one minute) immobilization of insect activity which leads from a moribund state to a state of kill. After 24 hours, the lice were again examined to determine the number killed. The results of this study are summarized in Table 1.

TABLE 1

Comparison of Pediculicidal Effects of
Spinosad in Shampoo at Various Concentrations

| | Mortality Data | |
| --- | --- | --- |
| Formulation | +1 hour % Knockdown | +24 hours % Mortality |
| Control | 0.2 | 1.0 |
| 10% spinosad/shampoo | 96.6 | 100.0 |
| 1% spinosad/shampoo | 48.0 | 100.0 |
| 0.1% spinosad/shampoo | 19.8 | 97.4 |
| 0.01% spinosad/shampoo | 14.7 | 35.5 |

The study showed that shampoo formulations containing 1% and 10% spinosad were highly effective pediculicides, providing a +24 hour mortality of 100%. The 10% concentration gave the quickest knockdown effect (96.6% at +1 hour), and even the 1% concentration provided a knockdown rate of 48%. The 0.1% spinosad/shampoo formulation was also an effective pediculicide, providing nearly 100% mortality after 24 hours.

I claim:

1. A pediculicidal shampoo comprising:
   (a) from about 0.1% to about 30% of a spinosyn, or a physiologically acceptable tetracyclic N-demethyl derivative or salt thereof;
   (b) from about 5% to about 30% of a synthetic surfactant;
   (c) from about 1% to about 7% of an amide; and
   (d) water.

2. A shampoo of claim 1 wherein the synthetic surfactant is anionic, amphoteric, cationic, zwitterionic, or non-ionic, or a mixture thereof.

3. A shampoo of claim 2 wherein the amide is coconut monoethanolamide or coconut diethanolamide or a mixture thereof.

4. A shampoo of claim 2 additionally comprising from about 1% to about 10% of a non-volatile silicone material.

5. A shampoo of claim 4 wherein the non-volatile silicone is a polyalkyl siloxane, polyalkylaryl siloxane or polyether siloxane co-polymer, or a mixture thereof, whose viscosity is from about 100 centipoise to about 150,000,000 centipoise at 25°.

6. A shampoo of claim 5 additionally comprising from about 0.5% to about 5% of a suspending agent selected from the group consisting of crystalline amphiphilic materials having needle-like or platelet structures, polymeric materials, clays and fumed metal oxides, or a mixture thereof.

7. A shampoo of claim 6 wherein the suspending agent is a crystalline amphiphilic material selected from the group consisting of long chain $C_{16}$–$C_{22}$ acyl derivatives and long chain $C_{16}$–$C_{22}$ alkanolamides of fatty acids, or a mixture thereof.

8. A shampoo of claim 7 wherein the suspending agent is an ethylene glycol diester.

9. A shampoo of claim 2 wherein the amount of a spinosyn, or tetracyclic N-demethyl derivative or salt thereof, is at a level from about 0.25% to about 1.5%.

10. A method for controlling a lice infestation in a human comprising topically administering to the human an effective amount of a formulation of spinosyn, or a physiologically acceptable tetracyclic N-demethyl derivative or salt thereof.

11. The method of claim 10 wherein the lice infestation is *Pediculus humanus capitis*.

12. The method of claim 10 wherein the lice infestation is *Pediculus humanus humanus*.

13. The method of claim 10 wherein the lice infestation is *Pthirus pubis*.

14. A method for treating human hair to kill and facilitate removal of lice and their eggs comprising the steps of:
   (a) applying from about 10 g to about 30 g of a formulation comprising a spinosyn, or a physiologically acceptable tetracyclic N-demethyl derivative or salt thereof, and a physiologically acceptable carrier to wet hair;
   (b) working the formulation through the hair and scalp;
   (c) leaving the formulation on the hair and scalp for about 6–10 minutes;
   (d) removing the formulation from the hair by rinsing, with water.

* * * * *

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 6,063,771 |
| (45) | ISSUED | : | May 16, 2000 |
| (75) | INVENTOR | : | Daniel Earl Snyder |
| (73) | PATENT OWNER | : | Eli Lilly and Company |
| (95) | PRODUCT | : | NATROBA® (spinosad) |

This is to certify that an application under 35 U.S.C. § 156 has been filed in the United States Patent and Trademark Office, requesting extension of the term of U.S. Patent No. 6,063,771 based upon the regulatory review of the product NATROBA® (spinosad) by the Food and Drug Administration. Since it appears that the requirements of the law have been met, this certificate extends the term of the patent for the period of

(94)                      1,494 days from June 22, 2019, the original expiration date of the patent, subject to the payment of maintenance fees as provided by law, with all rights pertaining thereto as provided by 35 U.S.C. § 156.

I have caused the seal of the United States Patent and Trademark Office to be affixed this 18th day of February 2015.

Michelle K. Lee
Deputy Under Secretary of Commerce for Intellectual Property and
Deputy Director of the United States Patent and Trademark Office

UNITED STATES PATENT AND TRADEMARK OFFICE
CERTIFICATE OF CORRECTION

PATENT NO. : 6,063,771

DATED : May 16, 2000

INVENTOR(S) : Daniel Earl Snyder

It is certified that an error appears in the above-identified patent and that said Letters Patent is hereby corrected as shown below:

In column 20, line 31, after "10. A method for controlling a lice infestation in a human..." insert --in need thereof--.

Signed and Sealed this

Fifteenth Day of May, 2001

Attest:

NICHOLAS P. GODICI

Attesting Officer     *Acting Director of the United States Patent and Trademark Office*